United States Patent [19]

Merkli

[11] Patent Number: 4,696,921

[45] Date of Patent: Sep. 29, 1987

[54] ANTIMALARIAL PHARMACEUTICAL COMPOSITIONS

[75] Inventor: Bernhard Merkli, Frenkendorf, Switzerland

[73] Assignee: Hoffmann-La Roche Inc., Nutley, N.J.

[21] Appl. No.: 549,377

[22] Filed: Nov. 7, 1983

Related U.S. Application Data

[63] Continuation-in-part of Ser. No. 331,360, Dec. 16, 1981, abandoned, which is a continuation of Ser. No. 122,645, Feb. 19, 1980, abandoned, which is a continuation of Ser. No. 904,958, May 11, 1978, abandoned.

[30] Foreign Application Priority Data

May 18, 1977 [LU] Luxembourg .......................... 77364

[51] Int. Cl.⁴ ................ A61K 31/635; A61K 31/505; A61K 31/47
[52] U.S. Cl. .................................. 514/157; 514/272; 514/314
[58] Field of Search .................... 424/229, 258, 251; 514/157, 272, 314

[56] References Cited

FOREIGN PATENT DOCUMENTS 28117 10/1972 Japan .
102825 9/1974 Japan .
26232 3/1976 Japan .
30675 3/1977 Japan .

OTHER PUBLICATIONS

Ohnmacht et al., J. Med. Chem., 14, pp. 926-928, (1971).
Peters, Bull. World Health Organ., 51, pp. 379-383, (1974).
Otten et al., Antibiotika Fibel, 4th Ed., 1975, pp. 953-961.
J. Med. Chem., 18, pp. 1122-1126, (1975).
Merkli et al., Acta Tropica, 37, 228-231, (1980).
Clinical Pharmacology and Therapeutics, 10 (1969), pp. 85-91.
A. P. Hall: British Medical Journal, 1 (1976), pp. 323-328.
T. R. Sweeney, Medical Research Reviews, 1 (1981), pp. 281-301.

*Primary Examiner*—Jerome D. Goldberg
*Attorney, Agent, or Firm*—Jon S. Saxe; Bernard S. Leon; Matthew Boxer

[57] ABSTRACT

Mixtures of active substances and pharmaceutical compositions useful in malaria therapy comprising a quinolinemethanol derivative of the formula

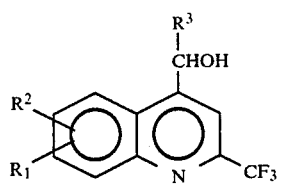

wherein $R^1$ is hydrogen, fluorine, chlorine, bromine, methyl or trifluoromethyl, $R^2$ is hydrogen, fluorine, chlorine, bromine, methyl or methoxy (at least one of $R^1$ and $R^2$ is other than hydrogen), and $R^3$ is $C_{1-6}$-alkylamino-$C_{1-3}$-alkyl, di-$C_{1-6}$-alkylamino-$C_{1-3}$-alkyl, 2-piperidyl or 3-piperidyl, or a pharmaceutically acceptable acid addition salt thereof; a compound which acts as a p-aminobenzoic acid antagonist; and a compound which acts as a dihydrofolic acid reductase inhibitor, are described.

5 Claims, 1 Drawing Figure

ANTIMALARIAL PHARMACEUTICAL COMPOSITIONS

BRIEF SUMMARY OF THE INVENTION

This is a continuation-in-part of Ser. No. 331,360, filed Dec. 16, 1981, now abandoned, which is in turn a continuation of Ser. No. 122,645, filed Feb. 19, 1980, now abandoned, which is a continuation of Ser. No. 904,958, filed May 11, 1978, now abandoned.

The invention relates to mixtures of active substances including pharmaceutical compositions for the treatment of malaria comprising a quinolinemethanol of the formula

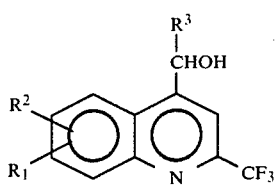

wherein $R^1$ is hydrogen, fluorine, chlorine, bromine, methyl or trifluoromethyl, $R^2$ is hydrogen, fluorine, chlorine, bromine, methyl or methoxy, provided that at least one of $R^1$ and $R^2$ is other than hydrogen, and $R^3$ is $C_{1-6}$-alkylamino-$C_{1-3}$-alkyl, di-$C_{1-6}$-alkylamino-$C_{1-3}$-alkyl, 2-piperidyl or 3-piperidyl, or a pharmaceutically acceptable acid addition salt thereof; a compound which is a p-aminobenzoic acid antagonist; and a compound which is a dihydrofolic acid reductase inhibitor. The pharmaceutical compositions comprise, in addition to a quinolinemethanol derivative, a p-aminobenzoic acid anatagonist, and a dihyrofolic acid reductase inhibitor, a pharmaceutical carrier therefor.

DETAILED DESCRIPTION OF THE INVENTION

Figure 1:
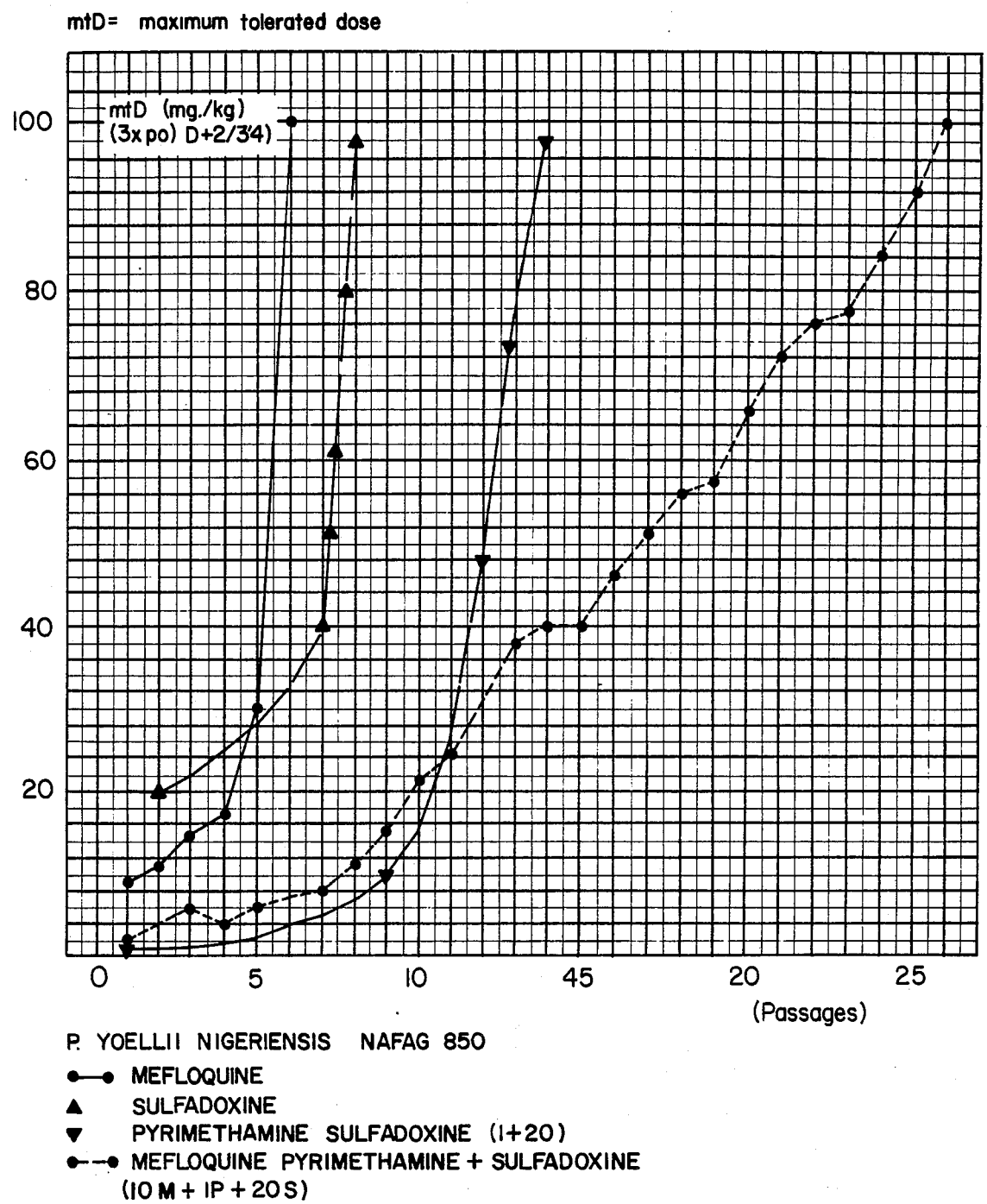

The simultaneous use of several active substances or ingredients having an antibacterial spectrum of activity in the treatment of bacterial infections has been known for a long time and has led to favorable results, for example, in the fight against tuberculosis. Further, it is possible in many cases to prevent or to severely inhibit the development of strains of causative organisms which are resistant to specific active substances. Investigations are turning to an increasing extent to the development of combination preparations. The combination of sulfonamides with dihydrofolic acid reductase inhibitors to give fixed combinations such as, for example, sulfamethoxazole with trimethoprim to give cotrimoxazole, permits the effective control of the causative organisms of bacterial infections, which organisms are already largely resistant not only to sulfonamides but also to antibiotics alone. With the combination sulfadoxine/pyrimethamine there has been developed an antimalarial agent, whose action depends on the mutual potentiation of the two components, and which is also effective against strains of causative organisms which are resistant to antimalarial agents such as chloroquine [7-chloro-4-(4-diethylamino-1-methylbutylamino)-quinoline] and other derivatives of 4-aminoquinolines or to pyrimethamine. The risk of the formation of resistance has now been reduced, by the present invention as hereinafter discussed, to an extent which has not hitherto been achieved with the aforementioned sulfadoxine/pyrimethamine combination.

Recently, mefloquine [erythro-α-2-piperidyl-2,8-bis(trifluoromethyl)-4-quinolinemethanol], a compound from the quinolinemethanol series, has been shown to be very suitable for the treatment of malaria, especially of tropical malaria. Furthermore, this compound exhibits good activity against chloroquine-resistant strains of *Plasmodium falciparum.* It is, however, to be feared that with the wide use of this compound, as well as of structurally analogous compounds from the quinolinemethanol series, there will also result relatively rapidly a resistance to these compounds, which would have a very negative effect on the future control of malaria in the world.

Since 1974 the situation worldwide in the field of malaria control has deteriorated, notwithstanding the intensive efforts of the WHO (World Health Organization). Malaria has increasingly spread in the majority of the countries, particularly in South East Asia and Latin America, so that, the number of chloroquine-resistant strains of the causative organism of tropical malaria, that is, *Plasmodium falciparum,* has increased to alarming proportions. The situation is made worse by the resistance of the transmitting mosquitoes to insecticides, for example, to DDT, which is already evident to some extent. Thus, the chloroquine-resistant *Plasmodium falciparum* strains further increase. Accordingly, there is an urgent objective in the fight against malaria to reduce the number of chloroquine-resistant causative organisms and to prevent their furtheer spread, namely, by means of medicaments which do not give rise to the development of resistance or contribute to a minimal development of resistance. By the development of combinations, which contain an quinolinemethanol derivative of formula I hereinafter which is active against malaria and a compound which acts as a p-aminobenzoic acid antagonist as well as a compound which acts as a dihydrofolic acid reductase inhibitor, the objective is approached to a considerable extent.

By way of background, it is noted that a preferred active substance mixture of the present invention, namely, mefloquine (base), sulfadoxine, and pyrimethamine (10:20:1 by weight) was published in the Bulletin of the World Health Organization 61(2) 169–178 (1983).

Also by way of background, it is noted that oral disclosure of a preferred active substance mixture of the present invention, namely, mefloquine (base), sulfadoxine, and pyrimethamine (10:20:1 by weight) was made at the Fifth International Congress of Parasitology in Toronto (Canada) Aug. 7–14, 1982.

The present invention provides active substance mixtures which consist of a quinolinemethanol derivative of the formula

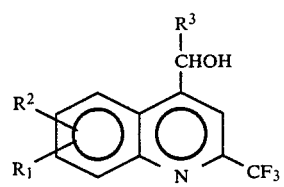

wherein $R^1$ is hydrogen, fluorine, chlorine, bromine, methyl or trifluoromethyl and $R^2$ is hydrogen, fluorine, chlorine, bromine, methyl or methoxy, provided that at least one of $R^1$ and $R^2$ is other than hydrogen, and $R^3$ is $C_{1-6}$-alkylamino-$C_{1-3}$-alkyl, di-$C_{1-6}$-alkylamino-$C_{1-3}$-alkyl, 2-piperidyl or 3-piperidyl, or a pharmaceutically acceptable acid addition salt of such a quinolinemethanol derivative; and a compound which acts as a p-aminobenzoic acid antagonist; as well as a compound which acts as a dihydrofolic acid reductase inhibitor. The invention also comprises pharmaceutical compositions based on said active substance mixtures and pharmaceutical carriers therefor.

The aforementioned p-aminobenzoic acid antagonist is preferably a sulfonamide or a sulfone, preferably sulfadoxine (4-sulfanilamido-5,6-dimethoxypyrimidine), sulfadimethoxine (6-sulfanilamido-2,4-dimethoxypyrimidine), 6-methoxy-4-sulfanilamidopyrimidine, sulfadiazine (2-sulfanilamidopyrimidine), sulfalene (2-sulfanilamido-3-methoxy-pyrazine), dapsone [bis(-4aminophenyl)-sulfone], acedapsone [bis(4-acetamidophenyl)-sulfone] or bis(4-formamidophenyl)-sulfone; sulfadoxine is especially preferred.

The aforementioned dihydrofolic acid reductase inhibitor is preferably proguanil, also known as $N^1$-(p-chlorophenyl)-$N^5$-isopropyldiguanide or, especially, pyrimethamine, also known as 6-ethyl-2,4-diamino-5-(p-chlorophenyl)-pyrimidine.

Chlorine is preferred among the halogen atoms referred to earlier in connection with the definition of $R^1$ and $R^2$ in formula I. $R^1$ and $R^2$ in formula I are preferably situated in the 6-, 7- and/or 8-position. Preferred $C_{1-6}$-alkylamino-$C_{1-3}$-alkyl groups are 2-($C_{2-4}$-alkylamino)-ethyl, especially 2-(tert. butylamino)-ethyl; and preferred di-$C_{1-6}$-alkylamino-$C_{1-3}$-alkyl groups are 2-(di-$C_{2-4}$-alkylamino)-ethyl, especially, 2-(dibutylamino)-ethyl. The 2-piperidyl group is the preferred piperidyl group.

The quinolinemethanol derivatives of formula I are known. To prepare the acid addition salts of the quinolinemethanol derivatives of formula I, especially of salts which can be used in pharmaceutical preparations, that is, physiologically compatible salts, there come into consideration inorganic and organic acids which are customarily used for this purpose, for example, hydrochloric acid, sulfuric acid, phosphoric acid, formic acid, acetic acid, oxalic acid, tartaric acid, maleic acid, benzoic acid, succinic acid, fumaric acid, levulinic acid, salicyclic acid, citric acid, isocitric acid, adipic acid, lactic acid, α-ketoglutaric acid, malic acid, malonic acid, glyceric acid, mevalonic acid, glucuronic acid, neuraminic acid, glutaric acid, aspartic acid, gluconic acid, mandelic acid, ascorbic acid, lactobionic acid, glucoheptonic acid, glutamic acid, nicotinic acid, pantothenic acid, folic acid, adenylic acid, geranylic acid, cytidylic acid and inosic acid.

Mefloquine and its acid addition salts, especially the hydrochloride, is especially preferred as the quinolinemethanol component. A combination of mefloquine, optionally in the form of an acid addition salt, preferably as the hydrochloride/sulfadoxine/pyrimethamine is the preferred active substance mixture provided by the present invention.

On the basis of the aforementioned active substance mixture, that is mefloquine hydrochloride/sulfadoxine/pyrimethamine, there is demonstrated hereinafter the improvement which can be achieved in malaria therapy with the active substance mixtures provided by the present invention and which results in the reduced development of resistance.

It will be appreciated from the discussion which follows that two preferred active substance mixtures of the present invention are mefloquine/sulfadoxine/pyrimethamine (10:20:1 by weight) and mefloquine hydrochloride/sulfadoxine/pyrimethamine (30:2:1 by weight).

A. The active substance mixture mefloquine hydrochloride/sulfadoxine/pyrimethamine (30:2:1by weight) was subjected to a test for the experimental development of resistant malaria strains in mice.

B. Method:

Albino mice (weighing 20 g.) were infected intravenously on day +0 with the N-strain of Plasmodium berghei (Keyberg 173) (injection dosage approximately $10^7$ parasitized erythrocytes) and treated on five successive days with the aforementioned active substance mixture. The first treatment was carried out 2-3 hours after the infection. On day +7 the infection was transmitted to new mice, which were treated in the same manner. The substance amount was thereby increased. This technique was used for all runs which follow. The donor mouse for the succeeding run must achieve on day +7 at least an erythrocyte infection rate (EIR) of approximately 10%. The mice were kept at an environmental temperature of 20±2° C. and received a standard mice diet and drinking water ad libitum. The active substance solution was freshly prepared each week, in most cases dissolved in an 0.5% aqueous carboxymethyl-cellulose solution or occasionally in distilled water, with addition of one drop of a polyoxyethylene-sorbitan fatty acid ester, and each mouse was given per os 0.2 ml. per treatment. The parasite infection was established on day +7 with the aid of Giemsa-colored blood smears.

The active substance mixture was tested for 36 weeks according to the method described earlier.

C. Results:

Table: Dosages of active substance mixture in mg/kg. (5×p.o.) tolerated by the N-stain of Plasmodium berghei, increase in the resistance after 24 or 36 runs.

| Active substance mixture | At the beginning of the experiment | After 24 runs | After 36 runs |
|---|---|---|---|
| Mefloquine hydrochloride/ sulfadoxine/ pyrimethamine (30:2:1) | 2 + 0.13 + 0.07 | 5 + 0.37 + 0.18 | 5.7 + 0.5 + 0.25 |

As is evident from the foregoing Table, the resistance to the active substance mixture investigated can increase. This increase is, however, comparatively small. After about 17 runs, an almost constant value was achieved and this hardly rose thereafter. The rapid achievement of a plateau, which was not foreseeable, establishes the great therapeutic advance obtainable with the active substance mixture mefloquine hydrochloride/sulfadoxine/pyrimethamine (30:2:1) provided by the present invention.

The active substance mixture of mefloquine, sulfadoxine and pyrimethamine (10:20:1 by weight) was subjected to tests for the experimental development of resistant malaria strains in mice.

The ability of the active substance mixture of the invention mefloquine, sulfadoxine, pyrimethamine (10:20:1 by weight) to inhibit the development of drug resistance by the rodent malaria parasite *P. yoellii nigeriensis* was compared to that of:

Erythro-α-2-piperidyl-2,8-bis(trifluoromethyl)-4-quinolinemethanol (Mefloquine);

4-Sulfanilamido-5,6-dimethoxypyrimidine (Sulfadoxine); and

A 20:1 mixture (by weight) of Sulfadoxine and 6-ethyl-2,4-diamino-5-(p-chlorophenyl)-pyrimidine (Pyrimethamine).

The methodology employed and results obtained when the active substances were tested for their ability to inhibit the development of drug resistance are as follows:

METHODOLOGY

Albino mice, strain Fullinsdorf SPF were fed on a diet of NAFAG 850 (containing a relatively high and variable PABA-content, 45–100 mg/kg) and tap water ad libitum. These mice were injected (i.p.) on D+0 (=day of infection) with approximately $10^7$ parasitized erythrocytes containing Plasmodium yoelii nigeriensis strain. The animals were administered either Active substance of the prior art or Active substance of the invention beginning on D+2 for 3 consecutive days. Blood films were made on D+7. On the same day blood was taken from a donor mouse of one of the treated groups showing a reasonable parasitemia, (i.e., 2–10% erythrocyte infection rate [EIR]. The dosage which yielded this EIR at each passage is plotted in the following figure as maximum tolerated dose [mtD]. The donor mouse blood was injected into a new group of mice. Drug dosage was gradually increased during successive passages.

RESULTS

It can be seen from the figure that drug resistance of the parasite, as reflected by the mtD, developed much more slowly when the subjects were administered the active substance of the invention, i.e. a combination of Mefloquine, sulfadoxine and pyrimethamine, than it did when the subjects were administered any of the active substances alone, i.e. Mefloquine, sulfadoxine or the potentiating combination of sulfadoxine and pyrimethamine.

The active substance mixtures provided by the present invention can be used as pharmaceutical preparations having direct or delayed liberation of the active ingredients in association with a compatible pharmaceutical carrier. Such carrier can be an organic or inorganic inert carrier material suitable for oral administration such as, for example, water, gelatin, gum arabic, lactose, starch, magnesium stearate, talc, vegetable oils, polyalkyleneglycols, or the like. The pharmaceutical preparations can be made up in a solid or liquid form, for example, as tablets, dragees, capsules, solutions or syrups. The pharmaceutical preparations may be sterilized and/or may contain further adjuvants such as preserving, stabilizing, wetting or emulsifying agents, flavor-improving agents, salts for varying the osmotic pressure or buffer substances. The pharmaceutical preparations can be prepared in a known manner.

The weight ratio of the individual components to one another in the active substance mixtures or the pharmaceutical compositions provided by this invention can vary within wide limits. It can be in the range of from 50:1 to 1:1, preferably between 20:1 and 2:1, for p-aminobenzoic acid antagonist to dihydrofolic acid reductase inhibitor, while the ratio of quinolinemethanol derivative of formula I to p-aminobenzoic acid antagonist plus dihydrofolic acid reductase inhibitor can be in the range of from 10:1 to 1:10, preferably between 10:1 and 1:3. A preferred weight ratio in the case of sulfadoxine to pyrimethamine is 20:1, the dosage unit for this case is 0.1–25 mg/kg., preferably 1–7 mg/kg. A preferred dosage unit for mefloquine hydrochloride in the mixture is in the range of from 1 to 15 mg/kg.

The active substance mixtures provided by the present invention as well as the pharmaceutical preparations based thereon are suitable not only for the curative treatment of all forms of malaria with an individual dosage in the form of, for example, one or more tablets, depending on the body weight of the warm-blood mammal and directions of the practitioner, but also for the prophylaxis and suppressive therapy in the sense of the WHO terminology at intervals of 1–4 weeks.

The following Examples illustrate pharmaceutical preparations containing the active substance mixtures provided by the present invention.

| Example 1 Tablets containing: | |
|---|---|
| Sulfadoxine | 500 mg. |
| Pyrimethamine | 25 mg. |
| Mefloquine (base) | 250 mg. |
| Maize starch | 100 mg. |
| Lactose | 100 mg. |
| Cellulose | 200 mg. |
| Polyvinylpyrrolidine | 130 mg. |
| Colloidal silicon dioxide | 6 mg. |
| Talc | 24 mg. |
| Magnesium stearate | 12 mg. |
| | 1347 mg. |

| Example 2 Tablets containing: | |
|---|---|
| Sulfadoxine | 300.0 mg. |
| Pyrimethamine | 15.0 mg. |
| Mefloquine hydrochloride | 109.65 mg. |
| Maize starch | 50.0 mg. |
| Lactose | 50.0 mg. |
| Cellulose | 99.35 mg. |
| Polyvinylpyrrolidone | 65.0 mg. |
| Colloidal silicon dioxide | 3.0 mg. |
| Talc | 12.0 mg. |
| Magnesium stearate | 6.0 mg. |
| | 710.00 mg. |

| Example 3 Tablets containing: | |
|---|---|
| Sulfadoxine | 100.0 mg. |
| Pyrimethamine | 5.0 mg. |
| Mefloquine hydrochloride | 36.5 mg. |
| Maize starch | 16.5 mg. |
| Lactose | 16.5 mg. |
| Cellulose | 33.0 mg. |
| Polyvinylpyrrolidone | 21.5 mg. |
| Colloidal silicon dioxide | 1.0 mg. |
| Talc | 4.0 mg. |
| Magnesium stearate | 2.0 mg. |
| | 236.0 mg. |

I claim:

1. An active substance mixture for the treatment or prophylaxis of malaria comprising erythro-α-2-piperidyl-2,8-bis(trifluoromethyl)-4-quinolinemethanol or a pharmaceutically acceptable salt thereof, sulfadoxine and pyrimethamine, in a weight ratio in the range of 10-30:2-20:1.

2. An active substance mixture for the treatment or prophylaxis of malaria comprising erythro-α-2-piperidyl-2,8-bis(trifluoromethyl)-4-quinolinemethanol, sulfadoxine and pyrimethamine in a respective weight ratio of about 10:20:1.

3. An active substance mixture for the treatment or prophylaxis of malaria comprising hydrochloride addition salt of erythro-α-2-piperidyl-2,8-bis(trifluoromethyl)-4-quinolinemethanol, sulfadoxine and pyrimethamine in a respective weight ratio of about 30:2:1.

4. A pharmaceutical composition for treatment or prophylaxis of malaria comprising an effective amount of erythro-α-2-piperidyl-2,8-bis(trifluoromethyl)-4-quinolinemethanol, sulfadoxine and pyrimethamine in a respective weight ratio of about 10:20:1 and a pharmaceutically acceptable carrier material.

5. A pharmaceutical composition for the treatment or prophylaxis of malaria comprising an effective amount of hydrochloride addition salt of erythro-α-2-piperidyl-2,8-bis(trifluoromethyl)-4-quinolinemethanol, sulfadoxine and pyrimethamine in a respective weight ratio of about 30:2:1 and a pharmaceutically acceptable carrier material.

* * * * *